United States Patent
Roeder et al.

(10) Patent No.: US 9,849,015 B2
(45) Date of Patent: Dec. 26, 2017

(54) ENDOLUMINAL PROSTHESIS INTRODUCER

(71) Applicant: Cook Medical Technologies LLC, Bloomington, IN (US)

(72) Inventors: Blayne A. Roeder, Bloomington, IN (US); Timothy A. Resch, Lund-Malmo (SE)

(73) Assignee: Cook Medical Technologies LLC, Bloomington, IN (US)

( * ) Notice: Subject to any disclaimer, the term of this patent is extended or adjusted under 35 U.S.C. 154(b) by 1011 days.

(21) Appl. No.: 14/136,720

(22) Filed: Dec. 20, 2013

(65) Prior Publication Data

US 2014/0188211 A1 Jul. 3, 2014

Related U.S. Application Data

(60) Provisional application No. 61/747,183, filed on Dec. 28, 2012.

(51) Int. Cl.
*A61F 2/06* (2013.01)
*A61F 2/966* (2013.01)
*A61F 2/97* (2013.01)

(52) U.S. Cl.
CPC ............ *A61F 2/966* (2013.01); *A61F 2/97* (2013.01)

(58) Field of Classification Search
CPC .. A61F 2/97; A61F 2/962; A61F 2/966; A61F 2002/9665; A61F 2002/9517
See application file for complete search history.

(56) References Cited

U.S. PATENT DOCUMENTS

| 5,254,107 | A | * | 10/1993 | Soltesz | A61M 25/005 |
| | | | | | 138/125 |
| 5,380,304 | A | | 1/1995 | Parker | |
| 5,755,775 | A | | 5/1998 | Trerotola et al. | |
| 6,159,198 | A | * | 12/2000 | Gardeski | A61M 25/0668 |
| | | | | | 604/161 |
| 6,287,329 | B1 | * | 9/2001 | Duerig | A61F 2/95 |
| | | | | | 606/198 |
| 6,478,813 | B1 | | 11/2002 | Keith et al. | |
| 6,485,513 | B1 | | 11/2002 | Fan | |

(Continued)

FOREIGN PATENT DOCUMENTS

| EP | 1844739 A1 | 10/2007 |
| EP | 2623151 A1 | 8/2013 |
| WO | WO 2012/043011 A1 | 4/2012 |

OTHER PUBLICATIONS

Extended European Search Report for EP 16171102.3 dated Aug. 19, 2016, 8 pages.

(Continued)

*Primary Examiner* — Tuan V Nguyen
(74) *Attorney, Agent, or Firm* — Brinks Gilson & Lione

(57) ABSTRACT

An endoluminal prosthesis introducer may include an elongate tubular sheath including a reinforced longitudinal segment and a peelable longitudinal segment extending distally from the reinforced segment. An elongate tubular cannula may be disposed within the sheath. Upon application of a force applied to a distal end of the sheath, the peelable segment may progressively split in a proximal direction, and the reinforced segment may longitudinally move relative to the cannula in a distal direction.

18 Claims, 8 Drawing Sheets

(56) References Cited

U.S. PATENT DOCUMENTS

| | | | |
|---|---|---|---|
| 6,533,811 B1 | 3/2003 | Ryan et al. | |
| 6,749,600 B1* | 6/2004 | Levy | A61M 25/0668 |
| | | | 604/324 |
| 7,314,481 B2* | 1/2008 | Karpiel | A61F 2/95 |
| | | | 600/585 |
| 2005/0113853 A1* | 5/2005 | Noriega | A61B 17/320758 |
| | | | 606/159 |
| 2007/0185558 A1* | 8/2007 | Hartley | A61F 2/95 |
| | | | 623/1.11 |
| 2007/0265694 A1* | 11/2007 | Sarac | A61F 2/95 |
| | | | 623/1.11 |
| 2008/0132989 A1* | 6/2008 | Snow | A61F 2/95 |
| | | | 623/1.12 |
| 2008/0215087 A1 | 9/2008 | Pavcnik et al. | |
| 2009/0024201 A1 | 1/2009 | Fitzgerald et al. | |
| 2009/0182411 A1* | 7/2009 | Irwin | A61F 2/966 |
| | | | 623/1.12 |
| 2009/0270969 A1 | 10/2009 | Fargahi et al. | |
| 2010/0268243 A1 | 10/2010 | Parker | |
| 2011/0066170 A1 | 3/2011 | Farnan | |
| 2012/0041537 A1* | 2/2012 | Parker | A61F 2/95 |
| | | | 623/1.11 |
| 2012/0059448 A1 | 3/2012 | Parker et al. | |
| 2012/0065725 A1 | 3/2012 | Glynn | |
| 2013/0053780 A1* | 2/2013 | Goode | A61B 17/3468 |
| | | | 604/164.05 |

OTHER PUBLICATIONS

Extended European Search Report dated Apr. 4, 2014 for EP 13275338 (6 pages).

Examination Report for corresponding EP Application No. 16171102.3 dated May 29, 2017, 7 pages.

* cited by examiner

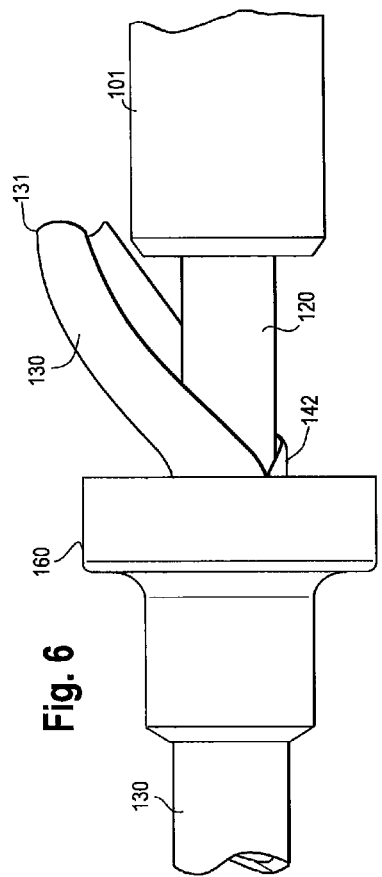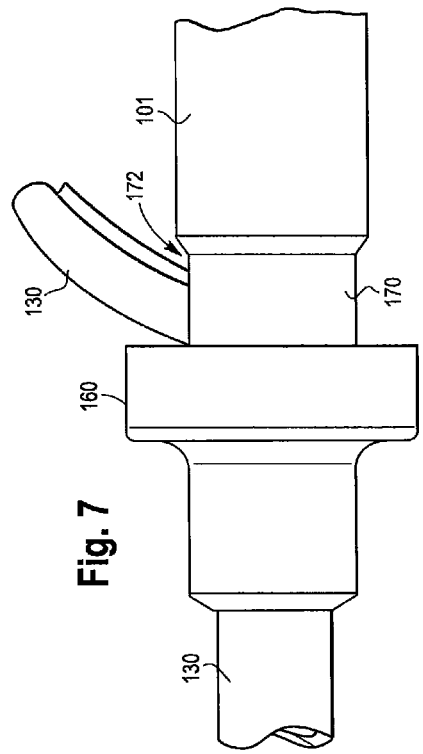

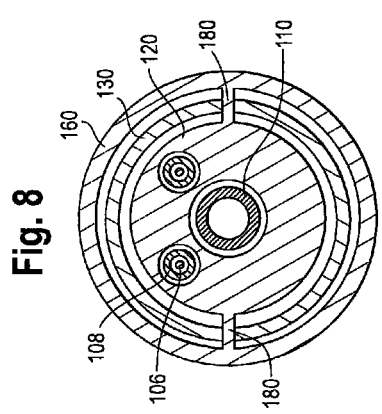
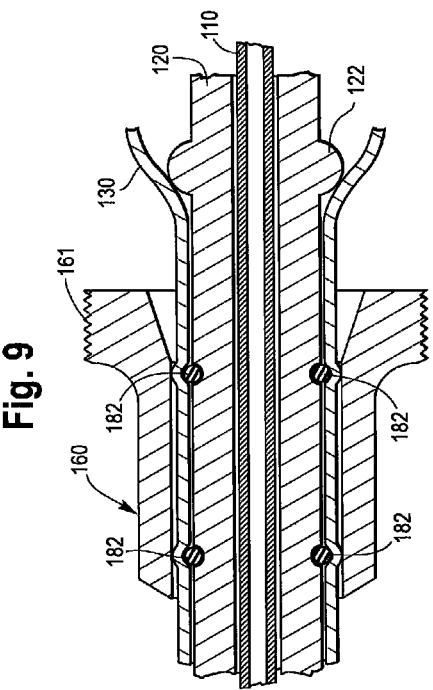

ENDOLUMINAL PROSTHESIS INTRODUCER

RELATED APPLICATION

The present application claims priority to U.S. Provisional Application Ser. No. 61/747,183 filed on Dec. 28, 2012, the contents of which application is herein incorporated by reference in its entirety.

TECHNICAL FIELD

This disclosure relates to medical devices and, more particularly, to an introducer for introducing an endoluminal prosthesis into a human or animal body.

BACKGROUND

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture.

One surgical intervention for weakened, aneurysmal, or ruptured vessels involves the use of a prosthetic device to provide some or all of the functionality of the original, healthy vessel, and/or preserve any remaining vascular integrity by replacing a length of the existing vessel wall that spans the site of vessel failure. For example, techniques have been developed for repairing abdominal aortic aneurysms by intraluminally delivering an endovascular graft to the aneurysm site through the use of a catheter-based delivery system. The endovascular grafts typically include a tube of pliable material (e.g., expanded polytetrafluoroethylene (ePTFE) or woven polyester) in combination with a graft anchoring component, which operates to hold the tubular graft in its intended position within the aorta. Most commonly, the graft anchoring component is formed of a stent or frame that is radially expandable to exert outwardly directing radial pressure against the surrounding blood vessel wall. The stent or frame can be either attached to or incorporated into the body of the tubular graft or provided separate from the graft and deployed within the graft.

It is preferable that these prostheses seal off the failed portion of the vessel. For weakened or aneurysmal vessels, even a small leak in the prosthesis may lead to the pressurization of, or flow in, the treated vessel which may aggravate the condition the prosthesis was intended to treat. A prosthesis of this type may be used, for example, to treat aneurysms of the abdominal aortic, iliac, or branch vessels, such as the renal, arteries.

A prosthetic device may be of unitary construction or may include multiple prosthetic modules. Modular systems typically are assembled in situ by overlapping the tubular ends of the prosthetic modules so that the end of one module sits partially inside the other module, preferably forming circumferential apposition through the overlap region. This attachment process is called "tromboning." The connections between prosthetic modules are typically maintained by the frictional forces at the overlap region and enhanced by the radial force exerted by the internal prosthetic module on the external prosthetic module where the two overlap. The fit may be further enhanced by stents fixed to the modules at the overlap region.

Endovascular treatment of aortic aneurysms can be simplified by use of preloaded components such as wires, catheters, and/or sheaths. These preloaded components can be preloaded into a delivery system (e.g., an introducer) and/or a prosthetic device prior to introduction into a patient to aid in delivery of additional prosthetic devices (e.g., branch extension prostheses) into the main prosthetic device. These preloaded components may help to simplify branch vessel cannulation, shorten procedural times, and/or provide improved outcomes for patients. The addition of preloaded components becomes more cumbersome as the length of the main body sheath of the delivery system is increased. For example, a preloaded delivery system with a 50 cm long main body sheath typically requires a 90 cm long preloaded component to traverse the lengths of the delivery system handle and the pusher catheter, through the distal portion of the main prosthetic device to a fenestration, and leave enough working length to access a target branch. Similarly, a preloaded delivery system with a 75 cm long main body sheath typically requires a 115 cm long preloaded component. Longer preloaded components may require additional catheters, wires, stents, or other elements. Moreover, longer preloaded components may be contrary to the intent behind the use of a preloaded system, which is to simplify delivery of the prosthetic device. For example, longer preloaded components may be significantly more difficult to control.

SUMMARY

In one example, an endoluminal prosthesis introducer may include an elongate tubular sheath including a reinforced longitudinal segment and a peelable longitudinal segment extending distally from the reinforced segment. An elongate tubular cannula may be disposed within the sheath. Upon application of a force applied to a distal end of the sheath, the peelable segment may progressively split in a proximal direction, and the reinforced segment may longitudinally move relative to the cannula in a distal direction.

In another example, a system may include an introducer and an endoluminal prosthesis loaded on the introducer. The introducer may include an elongate tubular sheath including a peelable longitudinal segment. An elongate tubular cannula may be disposed within the sheath. A handle may be positioned at a proximal end of the cannula. The prosthesis may include a tubular body having a lumen extending longitudinally within the tubular body. The prosthesis may be positioned about a proximal end of the cannula. In response to a pulling force applied to a distal end of the sheath, the peelable segment of the sheath may progressively split in a proximal direction, and the sheath may move longitudinally relative to the prosthesis between a delivery configuration in which the sheath is positioned over the prosthesis and a deployment configuration in which the sheath is positioned distal of the prosthesis. In the delivery configuration, the distal end of the sheath may be spaced longitudinally from a proximal end of the handle by a distance that is shorter than a length of the prosthesis.

In another example, a method of deploying an endoluminal prosthesis may include providing the prosthesis loaded on an introducer. The introducer may include an elongate tubular sheath and an elongate tubular cannula disposed within the sheath. The prosthesis may be disposed about a proximal end of the cannula and within the sheath. A peelable segment of the sheath may be progressively split by applying a pulling force to a distal end of the sheath. In response to progressively splitting the peelable segment of the sheath, a reinforced segment of the sheath positioned proximal of the peelable segment may be pulled distally relative to the prosthesis a sufficient distance to uncover the prosthesis.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIG. 6 illustrates an intermediate portion of one example of an introducer.

FIG. 7 illustrates an intermediate portion of one example of an introducer with a sheath retaining member attached to a handle via a coupling member.

FIG. 8 illustrates a transverse cross sectional view of one example of a sheath retaining member attached to a pusher catheter via a plurality of spokes.

FIG. 9 illustrates a longitudinal cross sectional view of one example of a sheath retaining member including a plurality of resilient members.

DETAILED DESCRIPTION OF THE DRAWINGS AND THE PRESENTLY PREFERRED EMBODIMENTS

The present disclosure relates to an introducer for introducing an endoluminal prosthesis into a human or animal body.

In the present disclosure, the term "proximal" refers to a direction that is generally closest to the heart during a medical procedure, while the term "distal" refers to a direction that is farthest from the heart during a medical procedure.

Figure 1:
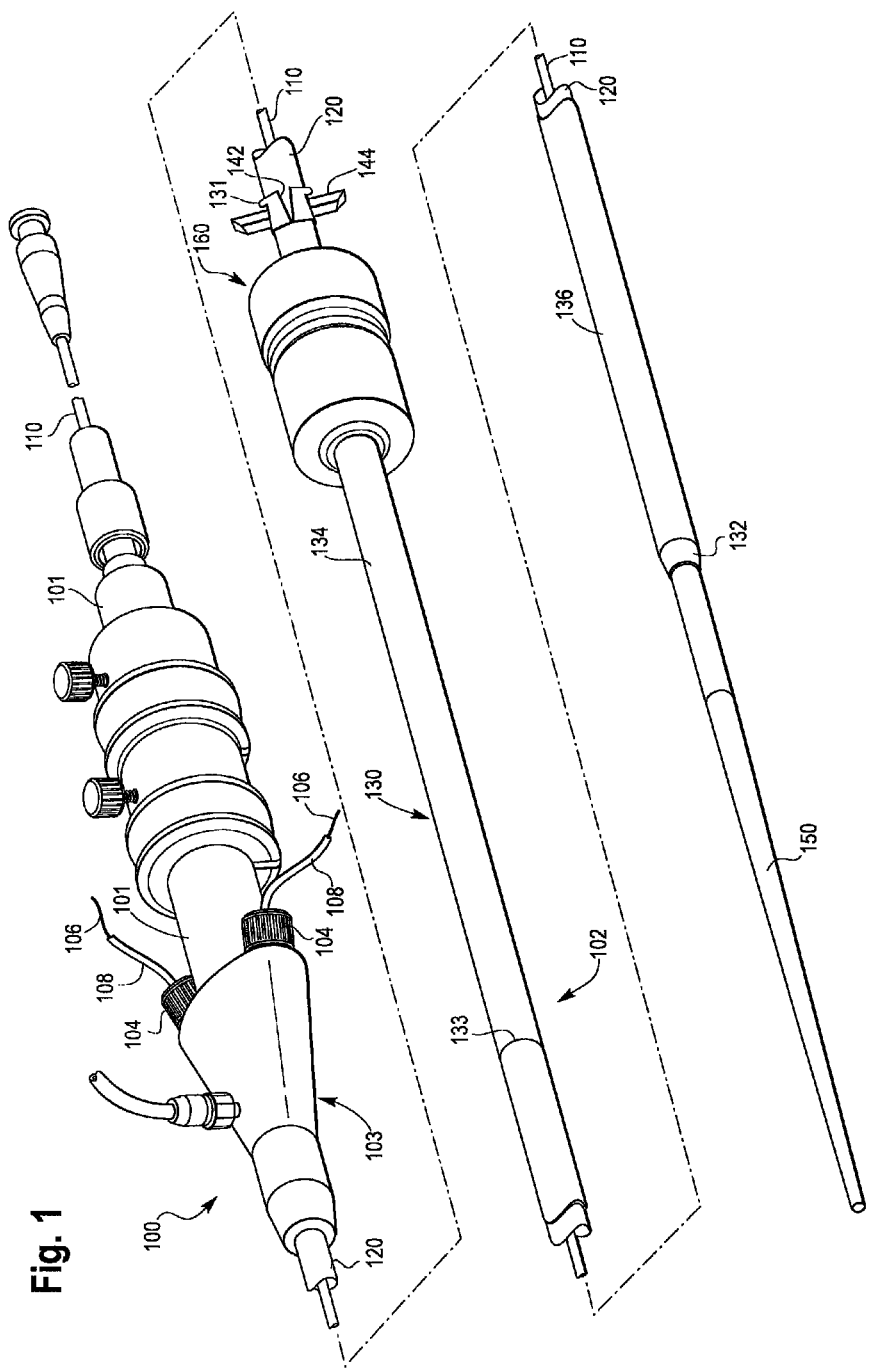
FIG. 1 illustrates one example of an introducer.
Figure 2:
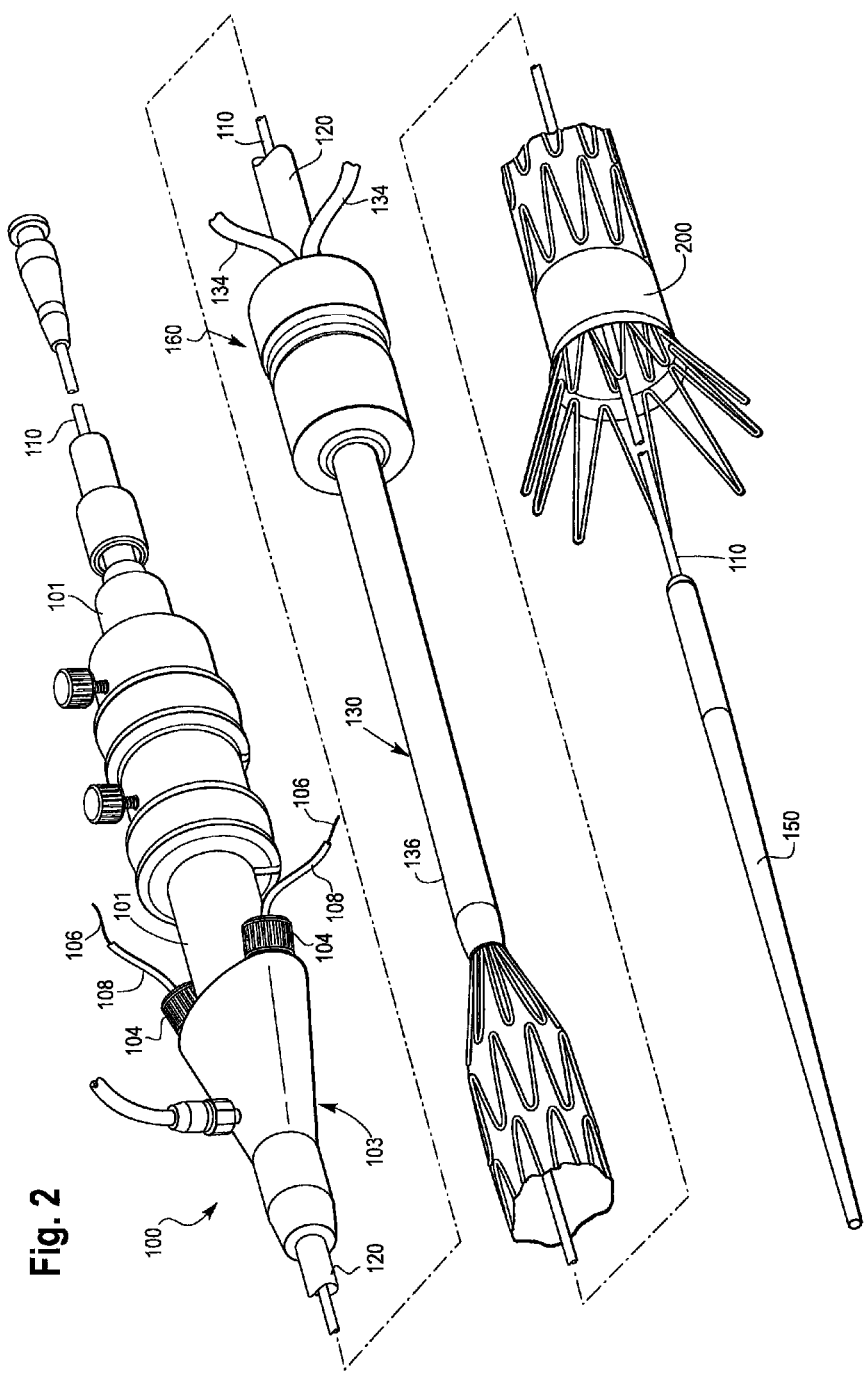
FIG. 2 illustrates the introducer of FIG. 1 with a sheath partially retracted to expose a prosthesis retained on the introducer.

FIGS. 1-2 illustrate one example of an introducer 100. The introducer 100 may be used to deliver and deploy an endoluminal prosthesis (e.g., a stent graft) as further described below. The introducer 100 may include a handle portion 101 and an introduction portion 102. The handle portion 101 may remain outside of the patient in use, and the introduction portion 102 may be introduced into the patient via a puncture in an artery such as a femoral artery. The introducer 100 may include an inner cannula 110, a catheter, such as a pusher catheter 120, disposed about the inner cannula, and/or a sheath 130 disposed about the inner cannula and/or the pusher catheter.

The inner cannula 110 may extend from a connector 112 (e.g., a Luer lock hub) positioned at the distal end of the introducer 100, through the handle 101 and the pusher catheter 120, and to a proximal tip 150. The inner cannula 110 may be configured as an elongate tubular member having a lumen extending longitudinally therein. The inner cannula 110 may extend at least partially through the proximal tip 150. Additionally, or alternatively, the proximal tip 150 may be coupled to the inner cannula 110. The inner cannula 110 may be tracked over a guide wire in a conventional manner to guide the introducer 100 through the vasculature of the patient. The connector 112 may be used to introduce liquids such as contrast media to enable tracking of the progress of an operation.

A prosthesis 200 may be disposed about the proximal end of the inner cannula 110 as shown in FIG. 2. The prosthesis 200 may have any suitable configuration known in the art. For example, the prosthesis 200 may be configured as a stent graft including a tubular graft body of a biocompatible material and a support structure (e.g., one or more stents) attached to the graft body. In one example, the prosthesis 200 may be configured for placement within a blood vessel (e.g., an aorta). The prosthesis 200 may include one or more fenestrations in the graft body. Branch extension prostheses may be placed in the fenestrations in a conventional manner to couple the prosthesis to one or more branch vessels (e.g., an iliac artery, renal arteries, a celiac artery, a superior mesenteric artery, a subclavian artery, an innominate artery, or a carotid artery). Although the prosthesis 200 will be described herein as a stent graft, this disclosure is not so limited. The prosthesis may be configured as, for example, a stent, a balloon, a filter (e.g., a vena cava filter), a coil (e.g., a cerebral aneurysm filler coil or an embolic coil), a valve (e.g., a venous valve), a bifurcated stent, a coronary vascular support frame, a urethral stent, a ureteral stent, a biliary stent, a tracheal stent, a gastrointestinal stent, an esophageal stent, or any other known device. Upon retraction of the sheath 130, the prosthesis 200 may expand (e.g., from a compressed configuration toward an expanded configuration) as shown in FIG. 2 for delivery of the prosthesis within the blood vessel or other body vessel. The prosthesis 200 may be self-expanding or balloon expandable.

The pusher catheter 120 may be configured as an elongate tubular member having a lumen extending longitudinally therein. The inner cannula 110 may be received within the lumen of the pusher catheter 120. The pusher catheter 120 may extend proximally from the handle 101. The proximal end of the pusher catheter 120 may be positioned near the distal end of the prosthesis 200. For example, the pusher catheter 120 may extend proximally from the handle 101 to a position near the distal end of the prosthesis 200 retained on the inner cannula 110.

The introducer 100 may be used as part of a preloaded system, which may include one or more auxiliary delivery components (e.g., guide wires and/or delivery catheters) preloaded in the introducer and the prosthesis 200 as further described below. To that end, the handle 101 may include a hub 103 positioned at the proximal end of the handle. The hub 103 may include one or more side ports configured to receive an auxiliary delivery component such as a guide wire and/or a delivery catheter. For example, the hub 103 may include two side ports 104 as shown in FIGS. 1-2. Each side port 104 may be in fluid communication with an auxiliary lumen extending longitudinally within the hub 103. For example, the hub 104 may include two auxiliary lumens, each in communication with a corresponding side port 104. Each auxiliary lumen of the hub 103 may be in fluid communication with a lumen of the pusher catheter 120. For example, the pusher catheter 120 may include two auxiliary lumens as shown in FIG. 8. Each auxiliary lumen of the pusher catheter 120 may be positioned adjacent to the main lumen of the pusher catheter (e.g., the lumen in which the inner cannula 110 may be received). Each auxiliary lumen of the pusher catheter 120 may be in communication with a corresponding auxiliary lumen of the hub 103.

An auxiliary delivery component such as a guide wire 106 may be received within each side port 104 and auxiliary lumen of the hub 104 and within each auxiliary lumen of the pusher catheter 120 as shown in FIGS. 1-2 and 8. In this manner, the guide wire 106 may extend proximally through the hub 103 and the pusher catheter 120 and into a lumen of the prosthesis 200. Additionally, or alternatively, an auxiliary delivery component such as a delivery catheter 108 may be received within each side port 104 and auxiliary lumen of the hub 104 and within each auxiliary lumen of the pusher catheter 120. The delivery catheter 108 may be positioned over the guide wire 106 and may extend proximally through the hub 103 and the pusher catheter 120 and into the lumen of the prosthesis 200. The guide wire 106 and/or the delivery catheter 108 may extend through one or more fenestrations in the prosthesis 200 to aid in cannulating a branch vessel for delivery of an extension prosthesis in any suitable manner (e.g., using conventional endovascular techniques).

Although the introducer 100 is described herein as including a hub having two side ports and two auxiliary lumens and a pusher catheter having two auxiliary lumens, the hub and/or the pusher catheter may include any other number of side ports and/or auxiliary lumens. Additionally, or alternatively, any number of auxiliary delivery components (e.g., guide wires 106 and/or delivery catheters 108) may be received within the hub and/or the pusher catheter. The description provided herein is equally applicable to introducers with hubs and/or pusher catheters having any number of side ports and/or auxiliary lumens and preloaded systems having any number of auxiliary delivery components.

The sheath 130 may be configured as an elongate tubular member having a sidewall 140 and a lumen extending longitudinally therein. The inner cannula 110 and/or the pusher catheter 120 may be slidably received within the lumen of the sheath 130. The sheath may include a distal end 131 and a proximal end 132 positioned opposite the distal end. In a delivery configuration, the distal end 131 of the sheath 130 may be positioned near the handle 101 as shown in FIG. 1 and further described below with reference to FIGS. 10-13. The sheath 130 may extend proximally to the proximal tip 150 for delivery of the prosthesis. The sheath 130 may be movable relative to the inner cannula 110, the pusher catheter 120, the handle 101, and/or the proximal tip 150 between the delivery configuration and a deployment configuration to at least partially expose the prosthesis 200 retained within the sheath and positioned about the inner cannula 110 at a prosthesis retention section near the proximal end of the introducer 100 as further described below. For example, FIG. 2 illustrates the sheath 130 partially retracted toward the deployment configuration to an intermediate configuration to partially deploy the prosthesis 200.

The sheath 130 may include a peelable segment 134 and a reinforced segment 136 as shown in FIGS. 1-2. The peelable segment 134 may be positioned distal of the reinforced segment 136. The peelable segment 134 may extend longitudinally between the distal end 131 of the sheath 130 and an intermediate point 133 of the sheath. For example, the peelable segment 134 may extend longitudinally from the distal end 131 to the intermediate point 133.

The peelable segment 134 may be peelable or splittable in a longitudinal direction to aid in retracting the sheath 130 to deploy the prosthesis as further described below. The reinforced segment 136 may extend longitudinally between the intermediate point 133 of the sheath 130 and the proximal end 132 of the sheath 130. For example, the reinforced segment 136 may extend longitudinally from the intermediate point 133 to the proximal end 132. The reinforced segment 136 may include a reinforcing member to enhance the dimensional stability and/or kink-resistance of the sheath as further described below.

The introducer 100 may include a sheath retaining member such as a valve 160 disposed about the sheath 130, the pusher catheter 120, and/or the inner cannula 110. The valve 160 may be positioned at the distal end of the introducer 100 near the handle 101 as shown in FIG. 1. The valve 160 may aid in maintaining the sheath 130 in close proximity to an outer surface of the pusher catheter 120 as further described below.

The peelable segment 134 of the sheath 130 may be progressively splittable in a distal to proximal longitudinal direction to retract the sheath relative to the inner cannula 110 and/or the pusher catheter 120. To that end, the peelable segment 134 may include at least one slit 142 in the sidewall 140 as shown in FIG. 1. The slit 142 may be positioned at the distal end 131 of the sheath 130. The slit 142 may be configured as a cut or notch formed in the sidewall 140. In response to a radially outward force being applied to the peelable segment 134, the slit 142 may be progressively extended proximally to split the peelable segment. To that end, the peelable segment may include one or more splitting guides. The splitting guide may extend longitudinally along the sidewall 140 from the slit 142. The splitting guide may be configured as a weakened area of the sidewall 140 along which the sidewall may be split to progressively extend the slit 142 as described herein. For example, the splitting guide may include a thinned region (e.g., a groove or a channel) formed in the sidewall, a tear strip embedded in the sidewall, a strip of material in the sidewall having a relatively lower tear resistance than the remainder of the sidewall, or any other feature configured to enable splitting of the sidewall. The peelable segment 134 may include at least one tab 144 positioned at the distal end 131 of the sheath 130 as shown in FIG. 1. The tab 144 may enable a physician to grasp the peelable segment 134 to apply the radially outward force to the peelable segment to retract the sheath 130 as further described below.

In one example, the peelable segment 134 may include two slits 142 and two tabs 144 as shown in FIG. 1. The slits 142 may be spaced from one another about the circumference of the sheath 130. For example, the slits 142 may be diametrically opposed from one another. The tabs 144 may be spaced from one another about the circumference of the sheath 130. For example, the tabs 144 may be diametrically opposed from one another. The tabs 144 may be positioned circumferentially between the slits 142. For example, each tab 144 may be spaced about 90 degrees from an adjacent slit 142 as shown in FIG. 1.

Applying a pulling force (e.g., a radially outward force) to the distal end 131 of the peelable segment 134 (e.g., by grasping the tabs 144 and pulling outward) may cause the peelable segment of the sheath 130 to split in a proximal direction (e.g., from the slit 144). Such splitting of the peelable segment 134 may cause a portion of the sidewall to split into two or more split portions positioned on opposite sides of the split from one another. In other words, each split portion may include a circumferential segment of the sidewall 140 and may be separated from an adjacent split portion by the split formed in the peelable segment 134.

The valve 160 may be held stationary relative to the handle 101, the inner cannula 110, and/or the pusher catheter 120 such that, as the split portions of the peelable segment 134 are pulled apart, the reinforced segment 136 of the sheath is pulled distally relative to the valve as shown in FIG. 2. The valve 160 may maintain the sheath 130 in close proximity to the pusher catheter 120 such that the split may be substantially unable to progress proximal of the valve. Continued application of the radially outward force to the split portions of the peelable segment 134 may cause the split portions of the peelable segment to engage the valve 160 (e.g., at the distal face and/or the inner surface of the valve), which may cause the portion of the sheath positioned proximal of the valve to be pulled distally. In this manner, the peelable segment 134 of the sheath may be progressively splittable in a proximal direction, and the reinforced segment 136 may be movable relative to the inner cannula 110, the pusher catheter 120, the handle 101, and/or the proximal tip 150 in a distal direction.

The radially outward force may be applied to the peelable segment 134 to split a sufficient length of the sheath 130 to expose the prosthesis 200. In other words, the reinforced segment 136 may be moved distally away from the proximal tip 150 a sufficient distance to expose the prosthesis 200. This may enable the prosthesis 200 to expand to deploy the prosthesis within the body vessel.

Figure 3:
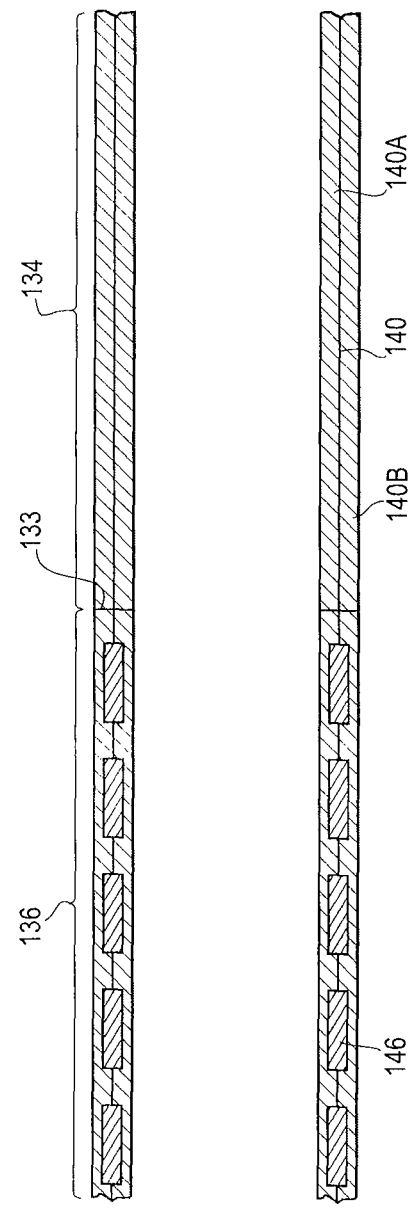
FIG. 3 illustrates a longitudinal cross sectional view of an intermediate portion of one example of a sheath.

FIG. 3 illustrates a longitudinal cross sectional view of an intermediate portion of the sheath 130. The sidewall 140 of the sheath 130 may be configured as an elongate tubular member having a lumen extending longitudinally therein. The sidewall 140 may be formed from any suitable material known in the art including, for example, polytetrafluoroethylene (PTFE) (e.g., TEFLON®, commercially available from E.I. DuPont De Nemours and Company, Wilmington, Del.), polyetheretherketone (PEEK), polyamide (e.g., nylon), or any other suitable polymeric or non-polymeric material. The sidewall may be formed from a single layer or multiple layers of material. For example, the sidewall 140 may include an inner layer 140A and an outer layer 140B as shown in FIG. 3. The inner layer 140A may be configured as an elongate tubular member having a lumen extending longitudinally therein. The outer layer 140B may be configured as an elongate tubular member having a lumen extending longitudinally therein. In one example, each of the inner layer 140A and the outer layer 140B may be configured as a length of tubing. The inner layer 140A may be positioned within the lumen of the outer layer 140B. The inner layer 140A and the outer layer 140B may be joined to one another to form the sidewall 140. The inner layer 140A and the outer layer 140B may be joined to one another by any suitable method known in the art including, for example, heat shrinking the outer layer over the inner layer, applying an adhesive between the inner layer and the outer layer, coextruding the inner layer and the outer layer, or any other suitable method. The inner layer 140A and the outer layer 140B may be formed from the same or different materials. Forming the sidewall 140 from multiple layers may aid in encapsulating a reinforcing member within the sidewall as further described below.

The sheath 130 may include the peelable segment 134 positioned distal of the intermediate point 133 and the reinforced segment 136 positioned proximal of the intermediate point as described above. The peelable segment 134 and the reinforced segment 136 may be formed integrally with one another (e.g., from a unitary tubular member) or formed separately and attached to one another (e.g., by bonding). The peelable segment 134 and the reinforced segment 136 may be formed from the same or different materials. For example, the portion of the sidewall 140 extending along the peelable segment 134 may be formed from a material having a lower resistance to tear propagation than the portion of the sidewall extending along the reinforced segment 136. In one example, the peelable segment 134 may be formed from an oriented Teflon material. This may aid in directing the split formed in the peelable segment 134 along the length of the sidewall 140. Additionally, or alternatively, the portion of the sidewall 140 extending along the peelable segment 134 may include the inner layer 140A and the outer layer 140B as shown in FIG. 3 and described above. Additionally, or alternatively, the portion of the sidewall 140 extending along the reinforced segment 134 may include the inner layer 140A and the outer layer 140B also as shown in FIG. 3 and described above. In some examples, the portion of the sidewall 140 extending along the peelable segment 134 may include a single layer, and the portion of the sidewall extending along the reinforced segment 136 may include multiple layers (e.g., the inner layer 140A and the outer layer 140B). Forming the peelable segment 134 from a single layer may aid in enabling the peelable segment to be split for retraction of the sheath 130 as described herein. Alternatively, the portion of the sidewall 140 extending along the peelable segment 134 may include multiple layers (e.g., the inner layer 140A and the outer layer 140B), and the portion of the sidewall extending along the reinforced segment 136 may include a single layer.

The reinforced segment 136 may include a reinforcing member 146 attached to the sidewall 140. The reinforcing member 146 may add dimensional stability and/or kink-resistance to the reinforced segment 136 of the sheath 130. The reinforcing member 146 may have any suitable configuration such as, for example, any of those described in U.S. Pat. No. 5,380,304 to Parker, which is incorporated by reference herein in its entirety. The reinforcing member 146 may extend circumferentially and/or longitudinally along the sidewall 140. In one example, the reinforcing member 146 may include a coil attached to the sidewall 140 as shown in FIG. 3. The coil may include a series of turns extending circumferentially and longitudinally along the sidewall 140 in a spiral or helical arrangement. The coil may be formed from a wire having a substantially rectangular cross sectional shape (e.g., a flat wire coil) as shown in FIG. 3. Use of a low profile coil having a flat wire construction may aid in minimizing the cross sectional profile (i.e., outer diameter) of the sheath 130. In other examples, the coil may be formed from a wire having a different cross sectional shape such as circular, triangular, elliptical, or any other polygonal or non-polygonal shape. The coil may be formed from any suitable material known in the art including, for example, a metal, a metal alloy (e.g., stainless steel or a shape memory or superelastic material such as nitinol), a multifilar material, or a composite material. The coil may be formed using any known technique including, for example, wrapping one or more wires around a mandrel, cutting the coil from a tubular cannula, or any other suitable technique. In other examples, the reinforcing member may have any other suitable configuration including, for example, a series of ring members, which may be attached to one another by longitudinal connector segments; a series of longitudinal wires, which may be attached to one another by circumferential connector segments; or any other configuration.

The reinforcing member 146 may be attached to the sidewall 140 in any suitable manner. For example, the reinforcing member 146 may be encapsulated within the sidewall 140 as shown in FIG. 3. To that end, the reinforcing member 146 may be positioned between the inner layer 140A and the outer layer 140B of the sidewall. In other words, the reinforcing member 146 may be laminated between the inner layer 140A and the outer layer 140B. Encapsulating the reinforcing member 146 within the sidewall 140 may enable inner and outer surfaces of the sidewall to be substantially smooth. The smooth outer surface of the sheath may aid in navigating the introducer 100 through the vasculature of the patient. The smooth inner surface of the sheath may aid in retracting the sheath longitudinally along the pusher catheter 120 as described herein.

Figure 4:
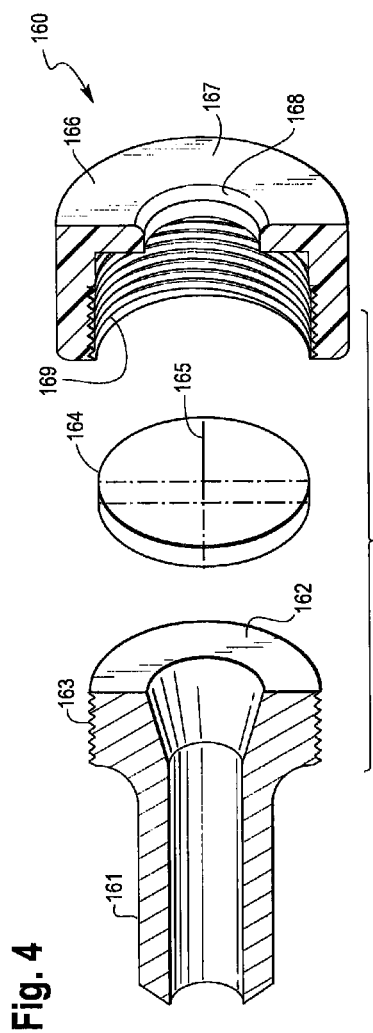
FIG. 4 illustrates a longitudinal cross sectional view of the components of one example of a sheath retaining member.
Figure 5:
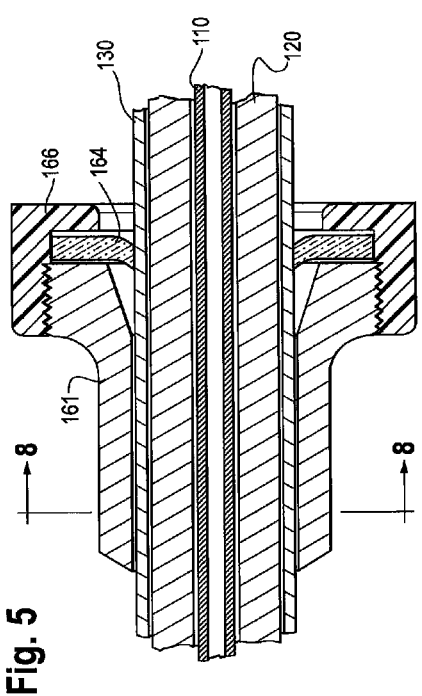
FIG. 5 illustrates a longitudinal cross sectional view of the sheath retaining member of FIG. 4 with an inner cannula, a pusher catheter, and a sheath disposed therein.

FIGS. 4-5 illustrate one example of the valve 160. The valve 160 may have any suitable configuration known in the art. For example, the valve 160 may include a valve body 161, a gasket 164, and a valve cap 166 as shown in FIGS. 4-5. The valve body 161 may be configured as a tubular member having a lumen extending longitudinally therein. The valve body 161 may include a distal face 162 configured to engage the gasket 164. The valve body 161 may include external threads 163 configured to engage the valve cap 166.

The gasket 164 may be configured as a disc-like member having an opening formed therein. The gasket may be formed from a unitary disc-like member or a plurality of gasket members (e.g., leaflets) arranged to collectively form a disc-like member. The opening may be configured as a slit 165 as shown in FIG. 4. Alternatively, the opening may be configured as a hole, a joint between adjacent gasket members, or any other type of opening. The gasket 164 may be sufficiently flexible that a medical device (e.g., the inner cannula 110, the pusher catheter 120, and/or the sheath 130) that is larger than the size of the opening may pass through the opening by deforming the gasket. In this manner, the gasket 164 may form a seal around the device disposed within the opening. In other examples, the gasket may be configured as a ring member (e.g., an O-ring) instead of or in addition to the disc-like member. The ring member may be received within the valve body 161 and/or between the valve body and the valve cap 166.

The valve cap 166 may be configured as a tubular member having a lumen extending longitudinally therein. The valve cap 166 may include an end plate 167 positioned at the distal end of the valve cap and including an aperture 168 formed therein. The aperture 168 may be configured to receive a medical device (e.g., the inner cannula 110, the pusher catheter 120, and/or the sheath 130) therein. The valve cap 166 may include internal threads 169 configured to engage the external threads 163 of the valve body 161. In other examples, the valve 160 may have any other suitable configuration known in the art.

FIG. 5 illustrates a longitudinal cross sectional view of the valve 160 with the inner cannula 110, the pusher catheter 120, and the sheath 130 received therein. The valve cap 166 may be threaded onto the valve body 161 such that the gasket 164 is clamped between the distal face 162 of the valve body and the end plate 167 of the valve cap. The gasket 164 may be deformed by the inner cannula 110, the pusher catheter 120, and the sheath 130 disposed therein as described above. The lumen of the valve body 161 may be flared (e.g., at the distal end of the lumen) to provide space for the deformed gasket 164. The deformed gasket 164 may exert a radially inward force on the sheath 130. In this manner, the gasket 164 may push the sheath 130 against the pusher catheter 120 to maintain the sheath against the outer surface of the pusher catheter. This may substantially prevent the portion of the sheath 130 engaged by the valve 160 from splitting (e.g., by preventing a radially outward force from being applied to the engaged portion of the sheath). In this manner, the split in the peelable segment 134 of the sheath 130 may be substantially prevented from progressing proximal of the valve 160 as described above.

FIG. 6 illustrates an intermediate segment of one example of the introducer 100 in which the sheath 130 has a single slit 142 formed at the distal end 131 thereof. The split portion of the sheath 130 may extend a sufficient distance distally and/or radially away from the valve 160 and/or the pusher catheter 120 that a physician may be able to grasp and pull on the split portion to apply the radially outward force to the sheath as described above. In this example, the tabs 144 may be omitted because the split portion of the sheath 130 may be sufficiently graspable to enable application of the radially outward force to the sheath. As the split portion of the sheath 130 is pulled outward away from the inner cannula 110 and/or the pusher catheter 120, the peelable segment 134 of the sheath 130 may be splittable in a proximal direction as described above with reference to FIG. 2. In this manner, the sheath 130 may be retracted to deploy the prosthesis.

In one example, the valve 160 may be attached to the handle 101 of the introducer 100 as shown in FIG. 7. To that end, the introducer 100 may include a coupling member 170 positioned between the handle 101 and the valve 160. The coupling member 170 may be configured as a tubular member having a lumen extending longitudinally therein. The inner cannula 110, the pusher catheter 120, and/or the sheath 130 may be received within the lumen of the coupling member 170. The distal end of the coupling member 170 may be attached to the handle 101. The proximal end of the coupling member 170 may be attached to the valve 160 (e.g., the valve cap 166 or the valve body 161). The coupling member 170 may be formed integrally with the handle 101 and/or the valve 160 (e.g., by molding). Alternatively, the coupling member 170 may be formed separately from the handle 101 and the valve 160 and joined thereto (e.g., by bonding). An aperture 172 may extend through the wall of the coupling member at a position between the distal end and the proximal end of the coupling member. The split portion of the sheath 130 may extend through the aperture 172 of the coupling member. In this manner, the split portion of the sheath 130 may be accessible such that a physician may grasp the split portion to apply the radially outward force to the peelable segment 134 of the sheath as described herein. The split portion of the sheath 130 may be pulled through the aperture 172 of the coupling member 170 to retract the sheath relative to the inner cannula 110 and/or the pusher catheter 120 as described herein. Although FIG. 7 illustrates the coupling member 170 used with the sheath shown in FIG. 6, the coupling member may be used with any other sheath configuration, including those shown in FIGS. 1-2. To that end, the aperture 170 may include a plurality of apertures (e.g., positioned diametrically opposed to one another) to receive a plurality of split portions and/or tabs 144.

The coupling member 170 may aid in fixing the valve 160 in place relative to the handle 101 so that the valve is substantially prevented from moving longitudinally relative to the handle during retraction of the sheath 130. The pusher catheter 120 may be attached to the handle 101 as described above. In this manner, fixing the valve 160 in place relative to the handle 101 may fix the valve in place relative to the pusher catheter 120. Accordingly, the valve may be substantially prevented from moving longitudinally relative to the pusher catheter 120 during retraction of the sheath 130.

FIG. 8 illustrates a transverse cross sectional view of one example of the introducer 100 taken along line 8-8 of FIG. 5. The valve 160 may be attached to the pusher catheter 120. To that end, the introducer 100 may include at least one spoke 180 extending radially between the valve 160 and the pusher catheter 120 as shown in FIG. 8. The spoke 180 may include an inner end attached to the pusher catheter 120 and an outer end attached to the valve 160. In this manner, the valve 160 may be fixed in place relative to the pusher catheter 120 so that the valve is substantially prevented from moving longitudinally relative to the pusher catheter and/or the handle 101 during retraction of the sheath 130. The spoke 180 may be disposed at any longitudinal position within the valve 160. For example, the spoke 180 may be longitudinally aligned with the valve body 161. The spoke 180 may be configured as a rib extending longitudinally along the valve body 161 and between the valve body and the pusher catheter 120. In another example, the spoke 180 may be longitudinally aligned with the valve cap 166. For example, the spoke 180 may be positioned within the aperture 168 and extend between the end plate 167 of the valve cap 166 and the pusher catheter 120. The spoke 180 may be circumferentially aligned with the split in the sheath 130. To that end, the introducer 100 may include two spokes 180 aligned with two splits in the sheath 130 (e.g., the sheath shown in FIGS. 1-2) as shown in FIG. 8. Alternatively, the introducer 100 may include a single spoke 180 aligned with a single split in the sheath 130 (e.g., the sheath shown in FIGS. 6-7). In other examples, the introducer may include any number of spokes aligned with any number of splits in the sheath.

The spoke 180 may be configured to aid in splitting the sheath 130 as the sheath passes through the valve during retraction of the sheath as described above. In other words, as the sheath 130 is pulled distally through the valve 160, the spoke 180 may aid in splitting the portion of the sheath positioned within the valve. To that end, the proximal edge of the spoke 180 may be sharpened (e.g., configured as a knife or blade) to cut through the sidewall 140 of the peelable segment 134 of the sheath 130 as the sheath passes through the valve 160.

FIG. 9 illustrates a longitudinal cross sectional view of one example of the valve 160 with the sheath 130, the pusher catheter 120, and the inner cannula 110 received therein. The valve 160 may include one or more resilient members 182. In one example, the valve 160 may include two resilient members as shown in FIG. 9. One resilient member 182 may be positioned near the distal end of the valve 160, and the other may be positioned near the proximal end of the valve. Alternatively, the valve may include any number of resilient members positioned at any longitudinal position within the valve. The resilient members 182 may at least partially encircle the sheath 130, the pusher catheter 120, and/or the inner cannula 110. To that end, the resilient members 182 may be configured, for example, as O-rings. The resilient members 182 may be deformable (e.g., expandable and/or compressible) to enable movement of the sheath 130 relative thereto. The resilient members 182 may be received within the lumen of the valve body 161. For example, the resilient members 182 may be positioned within the lumen of the valve body 161 and radially between the sheath 130 and the pusher catheter 120 as shown in FIG. 9. The resilient members 182 may push the sheath 130 radially outward against the inner wall of the valve body 161. The portion of the sheath 130 engaged by the resilient members 182 may be sandwiched between the resilient members and the valve body 161. This may aid in substantially preventing the split in the peelable segment 134 of the sheath 130 from travelling proximal of the valve 160 as described above.

The pusher catheter 120 may include one or more grooves in the outer surface thereof to receive the resilient members 182. For example, the pusher catheter 120 may include annular grooves extending at least partially circumferentially around the outer surface thereof. The resilient members 182 may be received in the grooves to aid in preventing the resilient members from translating longitudinally relative to the pusher catheter 120 (e.g., during retraction of the sheath 130).

In other examples, the resilient members 182 may be positioned radially between the sheath 130 and the valve 160. The resilient members 182 may push the sheath 130 against the pusher catheter 120 in a manner similar to that described with reference to the gasket 165 of the valve 160. This may aid in substantially preventing the split in the peelable segment 134 of the sheath 130 from travelling proximal of the valve 160 as described above.

Because the sheath 130 may be sandwiched between the resilient members 182 and the valve body 161 and/or between the resilient members and the pusher catheter 120, the gasket 164 and/or the valve cap 166 may be omitted as shown in FIG. 9. The valve 160 described in reference to FIG. 9 may be used in any of the examples described above with reference to FIGS. 1-2 and 6-8. Additionally, or alternatively, the valve 160 described in reference to FIG. 9 may be attached to the pusher catheter 120 and/or the handle 101 as described with reference to FIGS. 7-8. For example, the distal face 162 of the valve body 161 shown in FIG. 9 may be attached to the handle 101 via the coupling member 170 as described above with reference to FIG. 7. Additionally, or alternatively, the valve body 161 shown in FIG. 9 may be attached to the pusher catheter 120 via one or more spokes 180 (e.g., one or more ribs positioned longitudinally between the resilient members 182) as described above with reference to FIG. 8.

Additionally, or alternatively, the pusher catheter 120 may include one or more ridges 122 formed in the outer surface of the pusher catheter as shown in FIG. 9. The ridge 122 may be configured as a raised portion of the outer surface of the pusher catheter 120 that extends radially outward to a greater outer diameter than the adjacent portions of the pusher catheter. The outer diameter of the ridge 122 may be greater than the inner diameter of the valve 160 (e.g., the inner diameter of the valve body 161 and/or the inner diameter of the aperture 168 of the valve cap 166). The valve 160 may be substantially unable to move distally over the pusher catheter 120 beyond the ridge 120. In this manner, the ridge 122 may substantially prevent distal movement of the valve 160 during retraction of the sheath 130. Additionally, or alternatively, the pusher catheter may include one or more ridges positioned proximal of the valve 160 to substantially prevent proximal movement of the valve relative to the pusher catheter.

The outer diameter of the ridge 122 may be larger than the inner diameter of the sheath 130. In this manner, the ridge 122 may aid in splitting the sheath 130. For example, upon retraction of the sheath 130 distally relative to the pusher catheter 120 over the ridge 122, the ridge 122 may exert a radially outward force on the sheath. Such a radially outward force may split the sheath as described above. The pusher catheter 120 having one or more ridges 122 as described in reference to FIG. 9 may be used in any of the examples described above with reference to FIGS. 1-2 and 6-8.

The use of the sheath 130 having the peelable segment 134 may enable the introducer 100 to have a shorter total length than a conventional introducer. For example, deployment of a prosthesis using a conventional introducer typically involves retracting a sheath hub attached to the distal end of the sheath distally relative to the pusher catheter toward the handle. The sheath hub is retracted a sufficient distance toward the handle to expose the prosthesis. Accordingly, when the sheath is positioned over the prosthesis (e.g., for delivery of the prosthesis) the distance between the sheath hub and the handle typically must be at least as long as the prosthesis so that that sheath hub may be retracted at least the length of the prosthesis to expose the prosthesis for delivery. In other words, in the delivery configuration, an exposed portion of the pusher catheter of the conventional introducer is positioned outside of the sheath and between the sheath hub and the handle, and the exposed portion of the pusher catheter is at least as long as the prosthesis.

Figure 11:
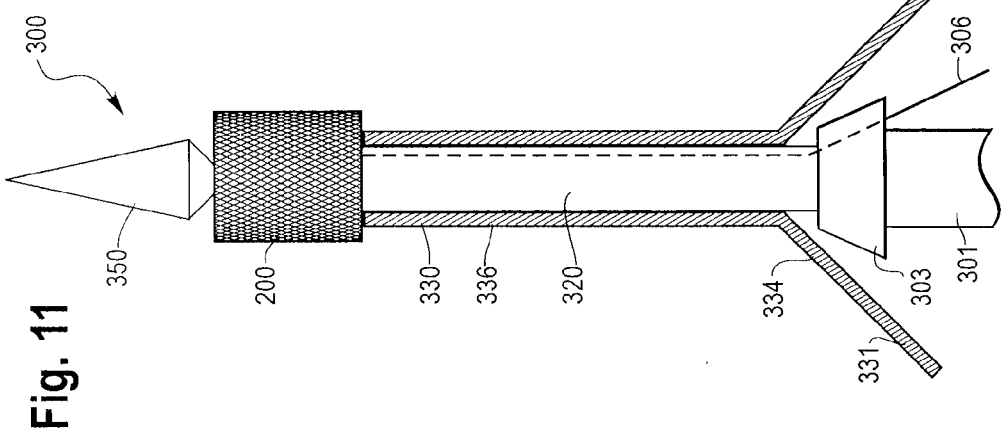
FIGS. 10-11 illustrate one example of an introducer in a delivery configuration and a deployment configuration, respectively.
Figure 10:
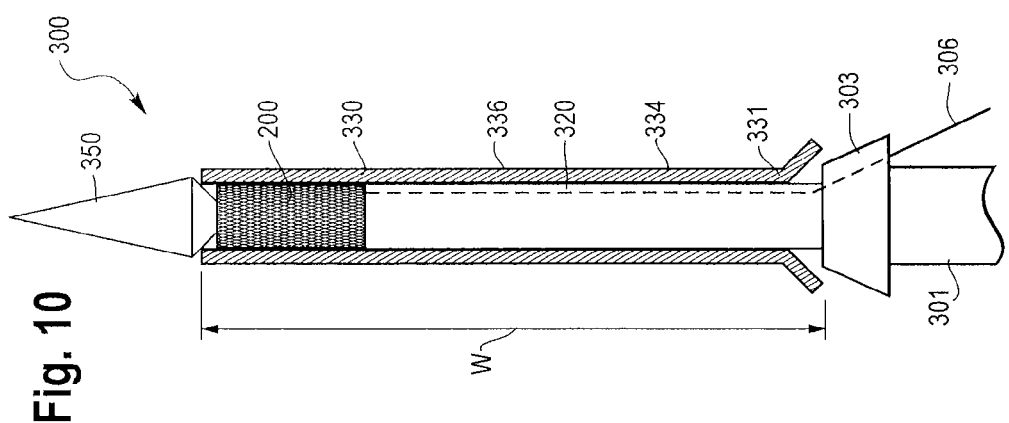

FIGS. 10-11 illustrate one example of an introducer 300 in the delivery configuration and the deployment configuration, respectively. The introducer 300 may be configured generally as described above with reference to the introducer 100. For example, the introducer 300 may include a handle 301, a pusher catheter 320 extending proximally from the handle, an inner cannula (not shown) extending within the handle and the pusher catheter, a proximal tip 350 positioned at the proximal end of the inner cannula, a sheath 330 extending over the inner cannula and the pusher catheter 320, and a valve (not shown) positioned about the sheath near the handle. The sheath 330 is shown in cross section in FIGS. 10-11. The sheath 330 may include a peelable segment 334 as described above with reference to the sheath 130. The sheath 330 may include a reinforced segment 336 positioned proximal of the peelable segment 334 also as described above with reference to the sheath 130. The handle 301 may include a hub 303 positioned at the proximal end thereof. An auxiliary delivery component 306 (e.g., a guide wire and/or a delivery catheter) may extend through the hub 303 and into the pusher catheter 320 as described above with reference to FIGS. 1-2. The prosthesis 200 may be positioned about the proximal end of the inner cannula as described above with reference to FIGS. 1-2.

In the delivery configuration, the distal end 331 of the sheath 330 may be positioned adjacent to the handle 301 as shown in FIG. 10. The distance between the distal end 331 of the sheath 330 and the handle 301 may be shorter than the length of the prosthesis. Thus, the distance between the distal end 331 of the sheath 330 and the handle 301 may be shorter than the distance between the sheath hub and the handle of a conventional introducer. The peelable segment 334 may be progressively splittable in a proximal direction as described above with reference to the sheath 130 to retract the sheath 330 distally relative to the inner cannula, the pusher catheter 320, the handle 301, the proximal tip 350, and/or the prosthesis 200 as shown in FIG. 11. The split portions of the peelable segment 334 of the sheath 330 may extend distally and/or radially outward beyond the handle 301 as shown in FIG. 11. In other words, the split portions of the peelable segment 334 may be withdrawn or retracted distally over the handle 301. In this manner, the sheath 330 may be retracted to expose the prosthesis 200 without the handle 301 interfering with retraction of the sheath. Because the split portions of the peelable segment 334 may extend distally and/or radially outward beyond the handle 301, it may be unnecessary to provide a longitudinal space between the distal end 331 of the sheath 330 and the handle in the delivery configuration.

In the delivery configuration, the distal end 331 of the sheath 330 may be positioned adjacent to the handle 301 as described above. In this manner, the length of the pusher catheter 320 may be shorter than the length of a conventional pusher catheter. For example, the pusher catheter 320 may be shorter than the conventional pusher catheter by a length that is approximately equal to the length of the prosthesis 200 (e.g., because such an excess length may not be required to retract the sheath relative to the pusher catheter). The reduced length of the pusher catheter 320 may enable the auxiliary delivery component 306 to have a reduced length relative to a conventional guide wire and/or delivery catheter (e.g., because the auxiliary delivery component may not be required to traverse the excess length of the conventional pusher catheter). Because longer sheaths, catheters, and/or wires are generally more difficult to control, the reduced length of the pusher catheter 320 and/or the auxiliary delivery component may enable improved control relative to a conventional introducer.

The introducer 300 may have a working length W extending from the proximal end of the handle 301 (e.g., the proximal end of the hub 303) to the proximal tip 350 (e.g., the distal end of the proximal tip) as shown in FIG. 10. The proximal end of the prosthesis 200 may be disposed at the distal end of the proximal tip 350. Additionally, or alternatively, the working length may extend from the proximal end of the handle 301 to the proximal end of the prosthesis 200. Additionally, or alternatively, the working length W may be approximately equal to the combined length of the pusher catheter 320 and the prosthesis 200. In one example, the sheath 330 may be substantially the same length as the working length W of the introducer 300. For example, the difference between the length of the sheath 330 and the working length W of the introducer 300 may be less than about 10 cm and/or less than about 5 cm. Additionally, or alternatively, the length of the sheath 330 may be between about 100% and about 110% and/or between about 100% and about 105% of the working length W of the introducer 300.

The reduced length of the pusher catheter 320 and/or the reduced working length W may enable the auxiliary delivery component 306 to have a reduced length relative to a conventional guide wire and/or delivery catheter. For example, the difference between the length of the auxiliary delivery component 306 and the length of the sheath 330 may be less than about 40 cm, less than about 30 cm, and/or less than about 20 cm. Additionally, or alternatively, the auxiliary delivery component 306 may be between about 30 cm and about 40 cm longer than the pusher catheter 320. Additionally, or alternatively, the length of the auxiliary delivery component 306 may be less than about 160%, less than about 150%, less than about 140%, and/or less than about 130% of the length of the sheath 330. In one example, the sheath 330 may have a length of between about 45 cm and about 55 cm, and the auxiliary delivery component 306 may have a length of between about 60 cm and about 70 cm. In one example, the sheath 330 may have a length of between about 55 cm and about 65 cm, and the auxiliary delivery component 306 may have a length of between about 70 cm and about 80 cm. In one example, the sheath 330 may have a length of between about 70 cm and about 80 cm, and the auxiliary delivery component 306 may have a length of between about 85 cm and about 95 cm. In one example, the sheath 330 may have a length of between about 80 cm and about 90 cm, and the auxiliary delivery component 306 may have a length of between about 95 cm and about 105 cm. In one example, the sheath 330 may have a length of between about 85 cm and about 95 cm, and the auxiliary delivery component 306 may have a length of between about 100 cm and about 110 cm. In one example, the sheath 330 may have a length of between about 95 cm and about 105 cm, and the auxiliary delivery component 306 may have a length of between about 110 cm and about 120 cm.

The peelable segment 334 and the reinforced segment 336 may have any suitable lengths. For example, the peelable segment 334 may have a sufficient length to enable retraction of the sheath 330 a sufficient distance to expose the prosthesis 200. To that end, the peelable segment 334 may have a length that is greater than or equal to the length of the prosthesis 200. In one example, the peelable segment 334 may be substantially the same length as the prosthesis. In one example, the peelable segment 334 may have a length of between about 30 cm and about 40 cm. The reinforced segment 336 may extend from the peelable segment 334 to the proximal end of the sheath 330.

Figure 13:
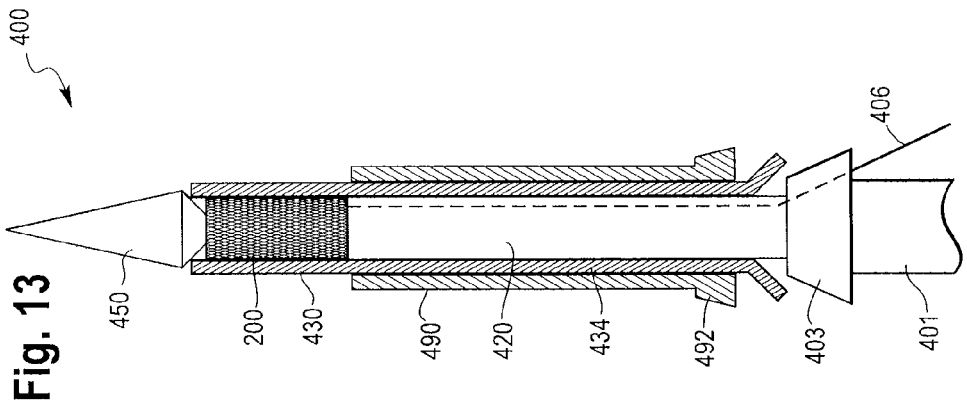
FIGS. 12-13 illustrate one example of an introducer in a delivery configuration and an intermediate configuration, respectively.
Figure 12:
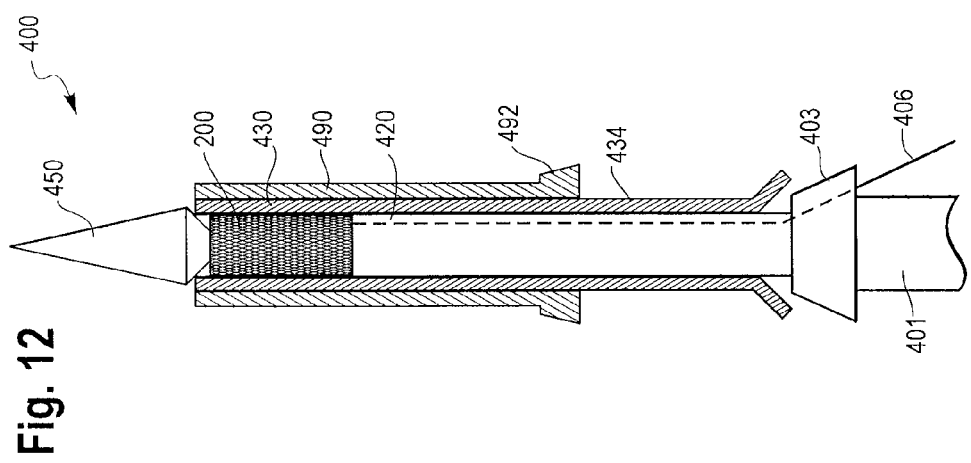

The sheath having the peelable segment and the reinforced segment may enable the pusher catheter to have a reduced length compared to a conventional introducer as described above, while providing sufficient stability (e.g., radial and/or longitudinal stability) and/or kink-resistance to withstand navigation through a body vessel. FIGS. 12-13 illustrate one example of an introducer 400 in the delivery configuration and an intermediate configuration, respectively. The introducer 400 may be configured generally as described above with reference to the introducers 100 and 300 except for the distinctions described below. For example, the introducer 400 may include a handle 401, a pusher catheter 420 extending proximally from the handle, an inner cannula (not shown) extending within the handle and the pusher catheter, a proximal tip 450 positioned at the proximal end of the inner cannula, and a sheath 430 extending over the inner cannula and the pusher catheter. The handle 401 may include a hub 403 positioned at the proximal end thereof. An auxiliary delivery component 406 (e.g., a guide wire and/or a delivery catheter) may extend through the hub 403 and into the pusher catheter 420 as described above with reference to FIGS. 1-2 and 10-12. The prosthesis 200 may be positioned about the proximal end of the inner cannula as described above with reference to FIGS. 1-2 and 10-12.

The introducer 400 may further include an outer sheath 490 extending over at least a portion of the sheath 430. The outer sheath 490 may include one or more reinforcing members (e.g., as described with reference to the reinforced segment 136). The outer sheath 490 may include a hub 492 positioned at the distal end thereof, and may extend proximally from the hub 492 to the proximal end of the sheath 430 as shown in FIG. 12. In this manner, the outer sheath 490 may provide stability (e.g., radial and/or longitudinal stability) and/or kink resistance to the introducer 400 for navigation through the body vessel.

The sheath 430 may include a peelable segment 434 as described above with reference to the sheaths 130 and 330. The sheath 430 may include a reinforced segment positioned proximal of the peelable segment 434 also as described above with reference to the sheaths 130 and 330. Alternatively, because the sheath 430 may be disposed within the outer sheath 490, the sheath 430 may be free of a reinforced segment as shown in FIGS. 12-13. In other words, the reinforced segment may be omitted from the sheath 430 (e.g., because the outer sheath 490 disposed about the sheath 430 may provide support and/or kink resistance to the introducer 400). Additionally, or alternatively, the introducer 400 may be free of a sheath retaining member (e.g., the valve 160 described above with reference to the introducer 100). For example, the sheath 430 may be disposed within and/or constrained by the outer sheath 490 instead of a sheath retaining member. Alternatively, the hub 492 of the outer sheath 490 may be configured as a sheath retaining member. For example, the hub 492 may be configured in a manner similar to those described above with reference to FIGS. 4-5 and 7-9.

The outer sheath 490 may be shorter than the sheath 430 so that, once the outer sheath reaches its maximum working distance, the sheath 430, the pusher catheter 420, the inner cannula, the handle 401, and/or the prosthesis 200 may be advanced proximally relative to the outer sheath 490 to track the introducer to its intended location and expose the proximal end of the sheath 430 as shown in FIG. 13. The hub 492 of the outer sheath 490 may be longitudinally spaced from the handle 401 a sufficient distance (e.g., at least the length of the prosthesis 200) to enable retraction of the outer sheath to expose the proximal end of the sheath 430 with the prosthesis retained therein. With the outer sheath 490 retracted, the sheath 430 may be progressively splittable in a proximal direction to retract the sheath 430 and deploy the prosthesis 200 as described above with reference to the introducers 100 and 300.

While various embodiments of the invention have been described, the invention is not to be restricted except in light of the attached claims and their equivalents. Drawings in the figures illustrating various embodiments are not necessarily to scale. Some drawings may have certain details magnified for emphasis, and any different numbers or proportions of parts should not be read as limiting unless so-designated in the present disclosure. Those skilled in the art will appreciate that embodiments not expressly illustrated herein may be practiced within the scope of the present invention, including those features described herein for different embodiments, which may be combined with each other and/or with currently-known or future-developed technologies while remaining within the scope of the claims presented herein. Moreover, the advantages described herein are not necessarily the only advantages of the invention and it is not necessarily expected that every embodiment of the invention will achieve all of the advantages described.

We claim:

1. An endoluminal prosthesis introducer comprising:
an elongate tubular sheath comprising a reinforced longitudinal segment and a peelable longitudinal segment extending distally from the reinforced segment; and
an elongate tubular cannula disposed within the sheath, wherein, upon application of a force applied to a distal end of the sheath, the peelable segment progressively splits in a proximal direction and the reinforced segment longitudinally moves relative to the cannula in a distal direction,
wherein the sheath comprises a tubular sidewall, and the reinforced segment of the sheath comprises a reinforcing member attached to the sidewall, and
wherein the peelable segment is free of the reinforcing member.

2. The introducer of claim 1, wherein the reinforcing member comprises a coil comprising a series of turns, and the coil is encapsulated within the sidewall and extends longitudinally along the reinforced segment of the sheath.

3. The introducer of claim 1, further comprising a proximal tip positioned at a proximal end of the cannula, and a handle positioned at a distal end of the cannula, wherein a working length of the introducer comprises a distance between the handle and the proximal tip.

4. The introducer of claim 3, wherein a difference between a length of the sheath and the working length of the introducer is less than about 10 cm.

5. The introducer of claim 1, further comprising a handle positioned at a distal end of the cannula, and an elongate tubular catheter positioned about the cannula, extending proximally from the handle, and disposed within the sheath.

6. The introducer of claim 1, further comprising a sheath retaining member comprising a tubular member comprising a distal end opening, a proximal end opening, and a lumen extending longitudinally within the sheath retaining member, wherein the sheath extends through each of the distal end opening and the proximal end opening of the sheath retaining member, and an engaged portion of the sheath is disposed within the lumen of the sheath retaining member.

7. The introducer of claim 6, wherein the sheath retaining member comprises a valve comprising a valve body, a valve cap engaged with the valve body, and a gasket captured between the valve body and the valve cap.

8. The introducer of claim 6, further comprising a handle positioned at a distal end of the cannula, and a tubular coupling member comprising a distal end attached to the handle and a proximal end attached to the sheath retaining member.

9. The introducer of claim 6, further comprising an elongate tubular catheter disposed about the cannula and within each of the sheath and the sheath retaining member, and a resilient member disposed within the sheath retaining member, at least partially encircling the catheter, and engaging the engaged portion of the sheath disposed within the lumen of the sheath retaining member.

10. The introducer of claim 6, further comprising an elongate tubular catheter disposed about the cannula and within each of the sheath and the sheath retaining member, and a spoke comprising an inner end coupled to the catheter and an outer end coupled to the sheath retaining member.

11. The introducer of claim 10, wherein the spoke comprises a plurality of spokes spaced from one another circumferentially around the catheter.

12. The introducer of claim 10, wherein the spoke comprises a sharpened proximal edge.

13. A system comprising:
an introducer and an endoluminal prosthesis loaded on the introducer;
the introducer comprising:
an elongate tubular sheath comprising a peelable longitudinal segment;
an elongate tubular cannula disposed within the sheath; and
a handle positioned at a proximal end of the cannula;
the prosthesis comprising a tubular body comprising a lumen extending longitudinally within the tubular body;
wherein the sheath comprises a tubular sidewall, and the reinforced segment of the sheath comprises a reinforcing member attached to the sidewall,
wherein the peelable segment is free of the reinforcing member,
wherein the prosthesis is positioned about a proximal end of the cannula, and, in response to a pulling force applied to a distal end of the sheath, the peelable segment of the sheath progressively splits in a proximal direction and the sheath moves longitudinally relative to the prosthesis between a delivery configuration in which the sheath is positioned over the prosthesis and a deployment configuration in which the sheath is positioned distal of the prosthesis; and
wherein, in the delivery configuration, the distal end of the sheath is spaced longitudinally from a proximal end of the handle by a distance that is shorter than a length of the prosthesis.

14. The system of claim 13, wherein the sheath comprises a reinforced longitudinal segment extending proximally from the peelable segment, in the delivery configuration, the reinforced segment is positioned over the prosthesis, and, in the deployment configuration, the reinforced segment is positioned distal of the prosthesis.

15. The system of claim 13, further comprising an elongate tubular catheter extending proximally from the handle and disposed about the cannula.

16. The system of claim 15, further comprising an auxiliary delivery component extending longitudinally within each of the handle and the catheter.

17. The system of claim 13, wherein the sheath is an inner sheath, and the introducer further comprises an outer sheath disposed about the inner sheath and comprising a sheath hub positioned at a distal end of the outer sheath, and the sheath hub is spaced longitudinally from the proximal end of the handle by a second distance that is at least as long as the length of the prosthesis.

18. A method of deploying an endoluminal prosthesis, the method comprising:
providing the prosthesis loaded on an introducer, the introducer comprising an elongate tubular sheath and an elongate tubular cannula disposed within the sheath, the prosthesis disposed about a proximal end of the cannula and within the sheath;
progressively splitting a peelable segment of the sheath by applying a pulling force to a distal end of the sheath; and in response to progressively splitting the peelable segment of the sheath, pulling a reinforced segment of the sheath positioned proximal of the peelable segment distally relative to the prosthesis a sufficient distance to uncover the prosthesis,
wherein the sheath comprises a tubular sidewall, and the reinforced segment of the sheath comprises a reinforcing member attached to the sidewall, and wherein the peelable segment is free of the reinforcing member.

* * * * *